United States Patent [19]

Yoo

[11] Patent Number: 5,624,460
[45] Date of Patent: Apr. 29, 1997

[54] NEEDLE FOR ACUPUNCTURE

[76] Inventor: Tae W. Yoo, 807, 1-Dong, Hanyang, Apt. 32-5, Banpo-dong, Seocho-ku, Seoul, Rep. of Korea

[21] Appl. No.: 554,254

[22] Filed: Nov. 6, 1995

[30] Foreign Application Priority Data

Jul. 19, 1995 [KR] Rep. of Korea .......... 95-17676

[51] Int. Cl.$^6$ .......................................... A61B 17/34
[52] U.S. Cl. .................. 606/189; 606/181; 606/204
[58] Field of Search .................. 606/189, 204, 606/181, 188, 185, 186, 167; 604/192, 194, 263

[56] References Cited

U.S. PATENT DOCUMENTS 3,905,375  9/1975  Toyama .......................... 606/189
3,976,078  8/1976  Toriello ......................... 606/189
5,089,001  2/1992  Hwang .......................... 606/189

*Primary Examiner*—Michael Powell Buiz
*Assistant Examiner*—Kevin Truong
*Attorney, Agent, or Firm*—Richard M. Goldberg

[57] ABSTRACT

A needle assembly for acupuncture includes a needle having a grip portion, and a needle head having a sharp end; a grip pipe made from paper, rubber or foamed resin, engaged around the needle head such that the sharp end of the needle extends out from the grip pipe; a guide pipe surrounding the needle and the grip pipe such that the grip pipe is positioned in a lower end of the guide pipe and the grip portion is positioned in an upper end of the guide pipe, with an upper portion of the grip portion extending out from the upper end of the guide pipe; and an adhesive membrane releasably connecting together the grip portion and an uppermost end of the guide pipe.

20 Claims, 3 Drawing Sheets

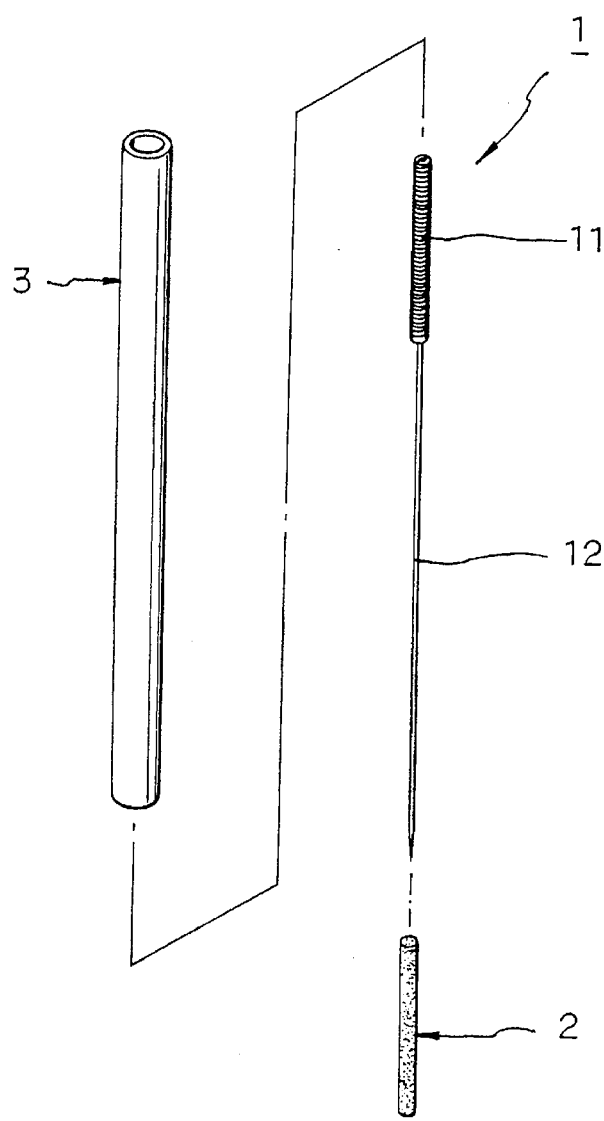
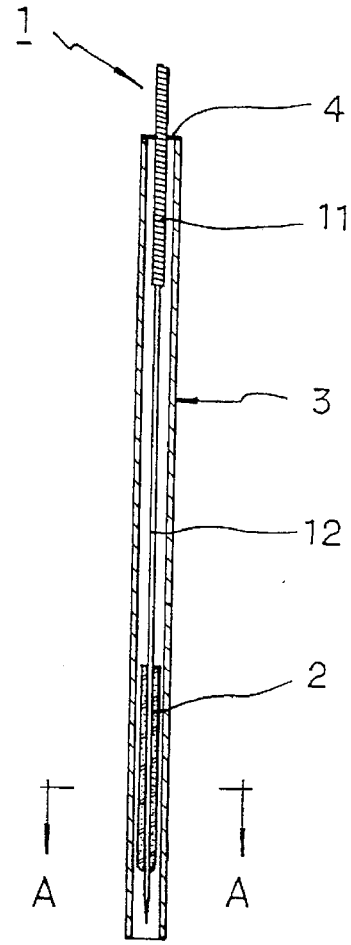
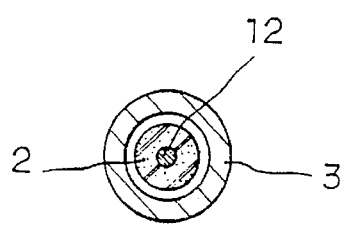

NEEDLE FOR ACUPUNCTURE

BACKGROUND OF THE INVENTION

1. Field of the Invention

The present invention relates to a needle for acupuncture having a grip pipe inserted over the needle head for pushing in easily and operating sanitarily when the needle for acupuncture is applied as acupuncture stimulus to an appected part or a region for acupuncture that is distributed along every part of the human body.

2. Description of the Prior Art

Conventionally, a needle assembly for acupuncture has been composed of plural needles and one guide pipe which were kept and carried. The needle for acupuncture was positioned at an appected part of the operation portion, by manually inserting the needle for acupuncture into a guide pipe. Then, the guide pipe was lifted up while grasping the needle head and an acupuncture stimulus was carried out. However, there was an unsanitary problem since the operation was handled by grasping the needle head with an unclean hand, and when pulling out the needle after the operation, it was not clean because blood stuck to the hand grasping the needle head. Thus, there were other disadvantages such as an outbreak of another disease occurring by an unsanitary secondary effect to the region for acupuncture or an appected part with the pollution generated during reoperation of the acupuncture by again using the needle head after wiping the needle head.

SUMMARY OF THE INVENTION

The present invention is designed to overcome the above said disadvantages of the prior art. An object of the present invention is to insert a grip pipe made of paper, rubber or foamed resin to the lower portion of the needle head, with the uppermost end of the guide pipe where the needle for acupuncture is inserted and the grip portion of the upper end of the needle for acupuncture being adhered by an adhesive membrane. Thus, carrying and keeping of the needle for acupuncture is very convenient as each needle for acupuncture is adhered by the adhesive membrane into the guide pipe, and at the time for operation, the needle for acupuncture is placed easily to the region for acupuncture of the human body or an appected part, and then the operation is carried out easily. Acupuncture stimulus is made by grasping the grip pipe simultaneously while lifting up the guide pipe. After the operation, there is no worry that blood is stuck to the hand when pulling out the grip pipe from the needle head, so there will be furnished the one time needle for acupuncture so that the operation can be done cleanly and sanitarily.

BRIEF DESCRIPTION OF THE DRAWINGS

FIG. 1 is an exploded perspective view of the present invention.

FIG. 2 is a sectional view of the present invention.

FIG. 3 is a sectional view of FIG. 2, taken along line A—A.

DESCRIPTION OF THE PREFERRED EMBODIMENTS

Figure 4:
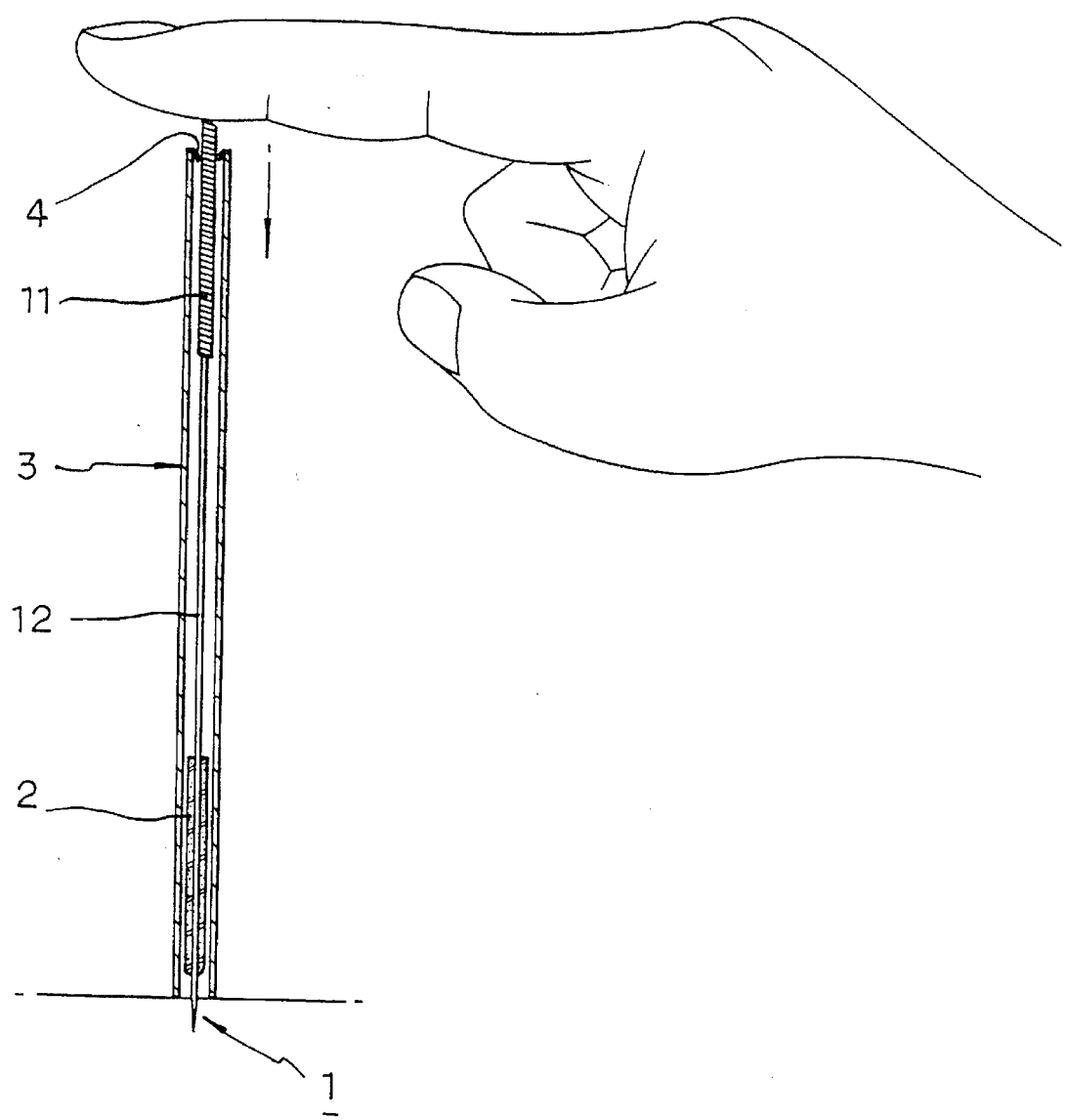
FIG. 4 is a sectional view showing the operating state of the present invention.

The present invention is described in detail with the accompanying drawings and examples.

A needle for acupuncture 1 is divided into a grip portion 11 and a needle head 12. A grip pipe 2 formed from paper, rubber or foamed resin is inserted to the lower end portion of the needle head 12. An adhesive membrane 4 is formed on the upper end portion a guide pipe 3 in which the needle for acupuncture 1 is inserted to fix grip portion 11 in guide pipe 3 for carrying purposes, such that the needle will not move in guide pipe 3.

In the present invention constructed as above, about 15–20 mm of the grip pipe 2 made of paper, rubber or foamed resin is inserted to a position of about 3–5 mm from the end portion of the needle head 12 of the needle for acupuncture 1, and the needle for acupuncture 1 is inserted into the guide pipe 3. By soaking part of the grip portion 11 in an adhesive agent can (not shown), and then forming the adhesive membrane 4 by adhering the uppermost end portion of the guide pipe 3 and a part of the grip portion 11, the needle for acupuncture 1 and the guide pipe 3 are integrated so that the keeping and carrying of the needle for acupuncture 1 is convenient.

Now the operating state for the above said present invention will be described in detail.

As shown in FIG. 4, after the needle for acupuncture 1, which is adhered integrally inside of the guide pipe 3 by the adhesive membrane 4 is correctly placed at a region for acupuncture of the human body or an appected part, and by knocking the upper end portion of the grip portion 11 of the needle for acupuncture 1 by one's hand, then the adhesive membrane 4 is destroyed or broken and the needle head 12 of the needle for acupuncture 1 is inserted to the body region or the appected part simultaneously with such breaking.

Figure 5:
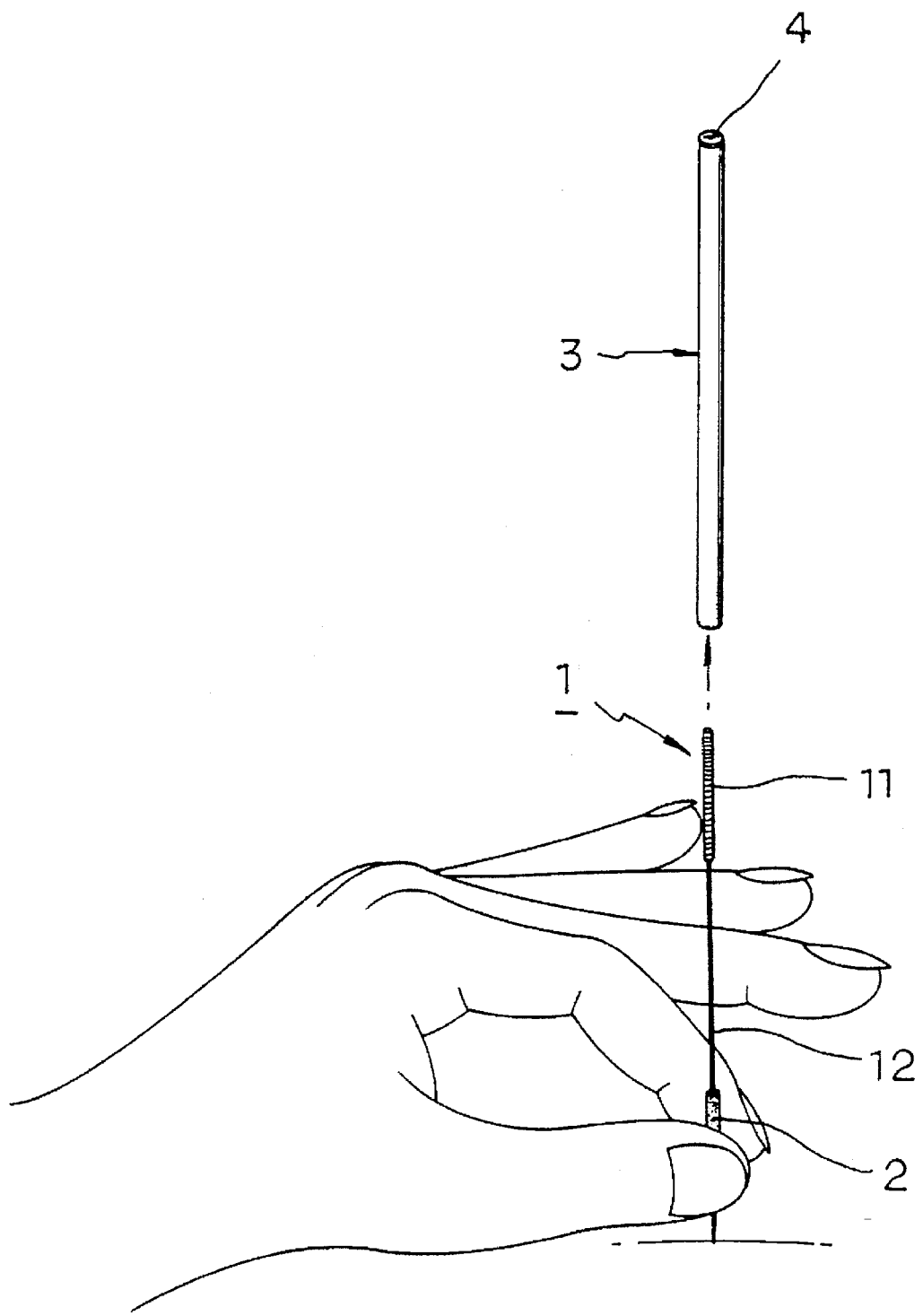
FIG. 5 is an exploded perspective view showing the operating state of the present invention.

As described above and as shown in FIG. 5, after separating the grip pipe 3 from the needle for acupuncture 1 by simultaneously grasping the grip pipe 2 which is inserted into the needle head 12 of the needle for acupuncture 1 and the guide pipe 3, guide pipe 3 is broken away completely. By rotating the grip pipe 2 while grasping the same with the hand or by giving an impact to the grip portion 11, the acupuncture operation is performed.

After the acupuncture operation is finished, by grasping the grip pipe 2 by hand, the needle for acupuncture 1 is broken away. At this time, if bad blood is discharged from the region for acupuncture or appected part, the blood is not stuck to the hand because of the grip pipe 2. Thus, a sanitary needle for acupuncture can be thrown away after finishing the acupuncture operation.

As described above, during the acupuncture operation, there is no worry about unsanitary operation by grasping the needle head 12 of the needle for acupuncture 1 with an unclean hand, so that it is very sanitary. Also, after finishing the operation, when pulling out the needle for acupuncture 1 from the region for acupuncture or the appected part, as the acupuncture operation is carried out by grasping the grip pipe 2 with the hand, there is an effect that bad blood is not stuck to the hand.

As described above in the present invention, the keeping and handling of the needle for acupuncture is very easy, and during the acupuncture operation, it is very sanitary as the acupuncture operation is carried out by grasping the grip pipe with the hand, and after the acupuncture operation, there is no worry about bad blood being stuck to the hand.

What is claimed is:

1. A needle assembly for acupuncture comprising:
   a needle including:
      a grip portion, and
      a needle head having a sharp end;

a grip pipe engaged around said needle head;

a guide pipe surrounding said needle and said grip pipe; and a release membrane releasably connecting together said grip portion and an upper end of said guide pipe.

2. A needle assembly for acupuncture according to claim 1, wherein said grip pipe is made from a material selected from the group consisting of paper, rubber and foamed resin.

3. A needle assembly for acupuncture according to claim 1, wherein said sharp end of said needle extends out from said grip pipe when said needle and grip pipe are surrounded by said guide pipe.

4. A needle assembly for acupuncture according to claim 1, wherein said release membrane is an adhesive membrane that releasably connects together an upper portion of said grip portion with an uppermost end of said guide pipe.

5. A needle assembly for acupuncture according to claim 1, wherein said grip pipe is positioned in a lower end of said guide pipe and said grip portion is positioned in an upper end of said guide pipe.

6. A needle assembly for acupuncture according to claim 1, wherein said grip pipe is positioned entirely within said guide pipe.

7. A needle assembly for acupuncture comprising:

a needle including:
 a grip portion, and
 a needle head having a sharp end;

a grip pipe engaged around said needle head;

a guide pipe surrounding said needle and said grip pipe, with said grip pipe being positioned in a lower end of said guide pipe and said grip portion being positioned in an upper end of said guide pipe, with an upper portion of said grip portion extending out from the upper end of said guide pipe; and a release membrane releasably connecting together said grip portion and an upper end of said guide pipe.

8. A needle assembly for acupuncture comprising:

a needle including:
 a grip portion, and
 a needle head having a sharp end;

a grip pipe engaged around said needle head such that said sharp end of said needle extends out from said grip pipe;

a guide pipe surrounding said needle and said grip pipe such that said grip pipe is positioned in a lower end of said guide pipe and said grip portion is positioned in an upper end of said guide pipe, with an upper portion of said grip portion extending out from the upper end of said guide pipe; and a release membrane releasably connecting together said grip portion and an upper end of said guide pipe.

9. A needle assembly for acupuncture according to claim 8, wherein said grip pipe is made from a material selected from the group consisting of paper, rubber and foamed resin.

10. A needle assembly for acupuncture according to claim 8, wherein said release membrane is an adhesive membrane that releasably connects together an upper portion of said grip portion with an uppermost end of said guide pipe.

11. A needle assembly for acupuncture comprising:

a needle including:
 a grip portion, and
 a needle head having a sharp end;

a grip pipe engaged around said needle head so as to be in contact with said needle head;

a guide pipe surrounding said needle and said grip pipe such that said grip pipe is positioned in a lower end of said guide pipe and said grip portion is positioned in an upper end of said guide pipe; and an adhesive membrane releasably connecting together said grip portion and an uppermost end of said guide pipe, wherein said needle head can be grasped via said grip pipe after said release membrane releases the connection of said grip portion and said guide pipe.

12. A needle assembly for acupuncture comprising:

a needle including:
 a grip portion, and
 a needle head having a sharp end;

a grip pipe engaged around said needle head;

a guide pipe surrounding said needle and said grip pipe such that said grip pipe is positioned in a lower end of said guide pipe and said grip portion is positioned in an upper end of said guide pipe with an upper portion of said grip portion extending out from the upper end of said guide pipe; and an adhesive membrane releasably connecting together said grip portion and an uppermost end of said guide pipe.

13. A needle assembly for acupuncture according to claim 11, wherein said sharp end of said needle extends out from said grip pipe.

14. A needle assembly for acupuncture according to claim 11, wherein said grip pipe is made from a material selected from the group consisting of paper, rubber and foamed resin.

15. A needle assembly for acupuncture according to claim 11, wherein said grip pipe is positioned entirely within said guide pipe.

16. A needle assembly for acupuncture comprising:

a needle including:
 a grip portion, and
 a needle head having a sharp end;

a grip pipe engaged around said needle head so as to be in contact with said needle head;

a guide pipe surrounding said needle and said grip pipe; and a release membrane releasably connecting together said grip portion and an upper end of said guide pipe, wherein said needle head can be grasped via said grip pipe after said release membrane releases the connection of said grip portion and said guide pipe.

17. A needle assembly for acupuncture according to claim 16, wherein said grip pipe is positioned entirely within said guide pipe.

18. A needle assembly for acupuncture according to claim 16, wherein said grip pipe is made from a material selected from the group consisting of paper, rubber and foamed resin.

19. A needle assembly for acupuncture according to claim 16, wherein said sharp end of said needle extends out from said grip pipe when said needle and grip pipe are surrounded by said guide pipe.

20. A needle assembly for acupuncture according to claim 16, wherein said grip pipe is positioned in a lower end of said guide pipe and said grip portion is positioned in an upper end of said guide pipe.

* * * * *